United States Patent
Kojima et al.

[11] Patent Number: 6,068,746
[45] Date of Patent: May 30, 2000

[54] OXYGEN SENSOR HAVING A SOLID ELECTROLYTE APPLICABLE TO AN INTERNAL COMBUSTION ENGINE

[75] Inventors: Takashi Kojima, Kasugai; Tomoyuki Kato, Nagoya; Makoto Hori, Oogaki; Masahiro Hamaya, Anjo; Minoru Ota, Okazaki, all of Japan

[73] Assignee: Denso Corporation, Kariya, Japan

[21] Appl. No.: 08/922,534

[22] Filed: Sep. 3, 1997

[30] Foreign Application Priority Data

Sep. 4, 1996 [JP] Japan ................................. 8-255475
Jul. 31, 1997 [JP] Japan ................................. 9-220895

[51] Int. Cl.[7] ..................................................... G01N 27/30
[52] U.S. Cl. ........................... 204/421; 204/427; 204/428
[58] Field of Search ..................................... 204/408, 421, 204/424, 425, 426, 431, 427, 428; 73/31.01, 31.02

[56] References Cited

U.S. PATENT DOCUMENTS

| 3,785,947 | 1/1974 | Baldwin et al. | 204/422 |
|---|---|---|---|
| 4,187,163 | 2/1980 | Steinke et al. | 204/428 |
| 4,818,364 | 4/1989 | Weber et al. | 204/425 |
| 4,948,491 | 8/1990 | Kato et al. | 204/427 |
| 5,522,979 | 6/1996 | Tatumoto et al. | 204/429 |
| 5,573,650 | 11/1996 | Fukaya et al. | 204/426 |
| 5,632,882 | 5/1997 | Wu | 205/783 |
| 5,670,032 | 9/1997 | Friese et al. | 204/424 |
| 5,679,226 | 10/1997 | Furusaki et al. | 204/424 |
| 5,711,863 | 1/1998 | Henkelmann et al. | 204/428 |
| 5,723,030 | 3/1998 | Renz | 204/427 |
| 5,900,129 | 5/1999 | Tsuji et al. | 204/427 |

FOREIGN PATENT DOCUMENTS

| 6-13488 | 4/1994 | Japan . |
|---|---|---|
| 6-331595 | 12/1994 | Japan . |
| 8-2514000 | 4/1996 | Japan . |

*Primary Examiner*—Elizabeth McKane
*Assistant Examiner*—Andrew Aldag
*Attorney, Agent, or Firm*—Pillsbury Madison & Sutro LLP

[57] ABSTRACT

An oxygen sensor element is inserted and fixed in a housing. A base body is provided at an end of the housing. The base body is made of a resin. The base body has a flange at an end. The housing has a caulking portion which is deformable when received a pressing force acting in a direction parallel to an axis of the oxygen sensor. By deforming the caulking portion, the flange is tightly connected with the caulking portion.

20 Claims, 10 Drawing Sheets

OXYGEN SENSOR HAVING A SOLID ELECTROLYTE APPLICABLE TO AN INTERNAL COMBUSTION ENGINE

BACKGROUND OF THE INVENTION

1. Field of the Invention

The present invention generally relates to an air-fuel ratio (e.g., oxygen concentration) sensor detecting an oxygen concentration of intake or exhaust gas in an intake or exhaust passage of an internal combustion engine. More specifically, the present invention relates to a structure of an oxygen sensor using a solid electrolyte.

2. Related Art

An adjustment of an air-fuel ratio in an internal combustion engine is very important for realizing the saving of energy (i.e., saving of fuel) and purification of exhaust gas. An oxygen sensor is used to detect the air-fuel ratio. A conventional oxygen sensor comprises a solid electrolyte which conducts oxygen ions. A pair of electrodes are provided on the inside and outside surfaces of a solid electrolyte. A gas anti-diffusion layer is added. They constitute an electrochemical cell serving as an oxygen sensor element. When the internal combustion engine is in an idling or start-up condition, the temperature of the exhaust gas is low. A heater unit is disposed inside the oxygen sensor. This heater is activated to increase the temperature of the oxygen sensor element when the internal combustion engine is in such an idle or start-up condition. Thus, the output of the oxygen sensor is stabilized.

More specifically, as shown in FIG. 15, an oxygen sensor 9 comprises a cup-shaped oxygen sensor element 91 serving as an electrochemical cell. The oxygen sensor element 91 is accommodated in a container 90 (refer to Japanese Patent 8-2514000). The container 90 comprises a housing 93 covering a front end of the oxygen sensor element 91 and a base body 92 located at a base end of the housing 93. A flange 931 is formed at a center of the housing 93. The flange 931 is fixed to an appropriate portion of an exhaust gas passage pipe. The oxygen sensor element 91 is fixed to the housing 93 via a talc 932.

An element protecting cover 935 is attached at a lower end (i.e., front end) of the housing 93. The element protecting cover 935 is inserted in the exhaust passage pipe and exposed to the exhaust gas. Atmospheric cover members 921 and 922 are provided at a base end side of the base body 92.

The atmospheric cover members 921 and 922 are made of metallic thin plates. The cover members 921 and 922 are installed to an upper end of the housing 93. The cover member 921 is fixed to the upper end of the housing 93 by caulking. Then, the cover member 922 is attached to the outer surface of the housing 93. Then, the cover member 921 and the cover member 922 are fixed each other by caulking.

A plurality of gas holes 936 are opened on the element protecting cover member 935. The gas holes 936 introduce the exhaust gas inside the element protecting cover member 935.

A heater unit 96 is inserted inside the oxygen sensor element 91. The heater unit 96 is supported by the oxygen sensor element 91. The oxygen sensor element 91 comprises a cup-shaped solid electrolyte. A reference electrode 94 and a measuring electrode 95 are provided on the opposed surfaces of the solid electrolyte. The electrodes 94 and 95 of the oxygen sensor element 91 are connected to signal output leads 940 and 950 via primary leads 941 and 951 and relay leads 945 and 955, respectively. The leads 940 and 950 serve as output terminals for transmitting the detection signals of the oxygen sensor element 91 to an external device, such as an engine control unit. The heater unit 96 is connected to a lead 960. Electric power is supplied to the heater unit 96 through the lead 960.

However, as described above, the base body of the conventional oxygen sensor is basically constituted by a plurality of cover members made of metallic thin plates. The structure of the above-described conventional base body is complicated. Installation of these cover members is troublesome and time-consuming.

SUMMARY OF THE INVENTION

In view of the above-described problems, the present invention has an object of providing an oxygen sensor having a base body easy to manufacture and easy to install.

In order to accomplish this and other related objects, the present invention provides an oxygen sensor having various aspects which will be described hereinafter. Reference numerals in parentheses, added in the following description, show the correspondence to the components described in preferred embodiments of the present invention. The reference numerals are thus merely used for the purpose of expediting the understanding of the present invention and not used for narrowly interpreting the scope of the present invention.

According to one aspect of the present invention, an oxygen sensor comprises a housing (41). An oxygen sensor element (10; 60) is inserted in the housing and fixed to the housing. A base body (45) is fixed to the housing. The base body is made of a resin.

The resin constituting the base body is preferably polyphenylene sulfide or phenol. The base body can be manufactured by a conventional injection molding, a compression molding or a transfer molding which are generally used for molding resin products.

The operations of the present invention will be explained hereinafter. According to the present invention, the base body (45) of the oxygen sensor (1; 5) is made of a resin. In general, the resin is easy to process. The base body (45) can be flexibly fabricated into a desirable configuration. Furthermore, the base body (45) can be manufactured as a single component, not a combination of a plurality of separate members. Accordingly, the base body (45) of the present invention is easy to install to the housing (41), compared with the conventional base body which is based on the combination of the plural members, such as thin metallic plates.

As described above, according to the above-described aspect of the present invention, it becomes possible to provide an oxygen concentration sensor having a base body which is easy to manufacture and easy to install.

According to features of preferable embodiments of the present invention, it is preferable that the base body (45) has a flange (450) at an end thereof and the housing (41) has a caulking portion (410) at an end thereof. The caulking portion (410) is deformable when receiving a pressing force (F) acting in a direction parallel to an axis of the oxygen sensor (1; 5). The flange (450) is thus fixed to the caulking portion (410) through a caulking operation.

The housing (41) is generally a metallic product. By employing the above-described structure, the metallic housing (41) and the resin base body (45) can be firmly caulked with each other maintaining an excellent sealing ability between them. Therefore, the moisture component existing outside the oxygen sensor (1; 5) can be surely prevented from entering inside the oxygen sensor.

Furthermore, it is preferable that the oxygen sensor element (10; 60) is connected to a first metallic terminal (27) used for outputting a detected sensor signal. The base body (45) is integral with the first metallic terminal (27). By integrating the base body (45) with the first metallic terminal (27), the oxygen sensor (1; 5) can be manufactured easily. The structure of the oxygen sensor can be simplified. An insert molding is preferably used for integrating the first metallic terminal (27) with the base body (45).

Moreover, it is preferable that the oxygen sensor element (10; 60) comprises a solid electrolyte (11), a measuring electrode (23) provided on an outer surface of a front end side of the solid electrolyte, and a first lead (24; 240) that is electrically conductive with the measuring electrode. The first lead (24; 240) of the oxygen sensor element is connected via a relay plate (32) to the first metallic terminal (27). A detected sensor signal is outputted through this first metallic terminal. And, the relay plate (32) is brought into contact with the first metallic terminal (27) by a pressing force acting in a direction normal to the axis of the oxygen sensor. With this arrangement, the first metallic terminal (27) can be elastically brought into contact with and fixed to the first lead (24; 240). Therefore, the connection between the first metallic terminal (27) and the first lead (24; 240) can be ensured.

Still further, it is preferable that an O ring (459) is interposed between the flange (450) and the caulking portion (410). With the provision of the O ring (459), an excellent sealing ability can be provided between the housing (41) and the base body (45).

Yet further, it is preferable that the oxygen sensor element (10) is configured into a cup shape. Alternatively, the oxygen sensor element (60) may be a laminated element. The above-described arrangements of the present invention are applicable to any oxygen sensor in which an oxygen sensor element is installed.

Furthermore, it is preferable that the oxygen sensor element (60) is a laminated element, a caulking portion (53) is integrally provided at an inner end of the housing (41). The oxygen sensor element (60) is fixed to the housing (41) by deforming this caulking portion (53) with a pressing force acting to a direction normal to the axis of the oxygen sensor. With this arrangement, the oxygen sensor element (60) can be fixed to the housing (41) while maintaining an excellent sealing ability between the oxygen sensor element (60) and the housing (41). Therefore, a stable sensor output can be obtained.

Preferably, a front end of the first metallic terminal (27) is configured into a flat plate, a wire, or a curved plate convex to a direction normal to the axis of the oxygen sensor.

With this arrangement, a plurality of metallic terminals can be disposed around the solid electrolyte. Accordingly, the base ends of the plurality of leads can be arrayed along the outer periphery of the solid electrolyte (11). Accordingly, the length of the solid electrolyte (11) can be shortened. Furthermore, the height of the oxygen sensor can be reduced. Thus, the oxygen sensor can be installed in a more narrow space.

Next, according to another aspect of the present invention, an oxygen sensor (1; 5) comprises a cup-shaped solid electrolyte (11) having an opening at a base end side and a bottom at a front end side. A measuring electrode (23) is provided on an outer surface of the front end side of the solid electrolyte. A reference electrode (21) is provided on an inner surface of the front end side of the solid electrolyte. A first lead (24; 240) is brought into electrical contact with the measuring electrode and extends to the base end side of the solid electrolyte. A second lead (22; 220) is brought into electrical contact with the reference electrode and extends to the base end side of the solid electrolyte. A housing (41) has a through hole for accommodating the solid electrolyte. A base body (45) is fixed to the housing and covers the base end side of the solid electrolyte. A first metallic terminal (27) is brought into electrical contact with the first lead and extends to a base end of the base body. A second metallic terminal (26) is brought into electrical contact with the second lead and extends to the base end of the base body. And, a front end of the first metallic terminal is configured into a flat plate, a wire, or a curved plate convex to the axis of the solid electrolyte. The front end of the first metallic terminal is thus brought into contact with the first lead by a pressing force acting toward the axis of the solid electrolyte.

According to the above-described aspect of the present invention, the front end of the first metallic plate is, for example, a flat plate. A signal output portion of the first lead is formed into an arc shape along the outer surface of the base end side of the cylindrical solid electrolyte. The front end of the first metallic terminal pushes the signal output portion toward the axis of the solid electrolyte. Furthermore, the signal output portion may be dislocated with respect to the solid electrolyte in a radial direction or a perpendicular direction (i.e., a tangential direction on the surface of the solid electrolyte) of the solid electrolyte. Even in such a condition, imperfect contact is not caused between the first metallic terminal and the first lead. This effect can be enjoyed similarly when the front end of the first metallic plate is a wire or a curved plate convex to the axis of the solid electrolyte.

Furthermore, when the front end of the first metallic terminal is configured into a flat plate, a wire, or a curved plate convex to the axis of the solid electrolyte, it becomes possible to dispose many metallic terminals. Accordingly, the base ends of the leads are arrayed along the outer periphery of the solid electrolyte. As a result, the length of the solid electrolyte can be shortened.

According to the features of the preferred embodiments of the present invention, it is preferable that an end (221) of the second lead (22) is exposed on an outer surface at the base end side of the solid electrolyte. A front end of the second metallic terminal (26) is configured into a flat plate, a wire, or a curved plate convex to the axis of the solid electrolyte. The front end of the second metallic terminal is brought into contact with the second lead by a pressing force acting toward the axis of the solid electrolyte.

Moreover, it is preferable that an electric heater (35) is located on an outer surface of the solid electrolyte. Third metallic terminals (28, 29) are brought into electrical contact with the electric heater and extend to the base end of the base body. And, a front end of each third metallic terminal is configured into a flat plate, a wire, or a curved plate convex to the axis of the solid electrolyte. The front end of the third metallic terminal is brought into contact with the electric heater by a pressing force acting toward the axis of the solid electrolyte.

The base ends (i.e., signal output portion) of the first and second leads and the base end (i.e., power supply portion) of the electric heater can be arrayed along the outer periphery of the solid electrolyte. Thus, the length of the solid electrolyte can be shortened.

Still further, it is preferable that the oxygen sensor element (10; 60) is held, at the front end of the first metallic terminal, to the housing (41) by a pressing force acting toward the axis of the solid electrolyte. With this arrangement, the oxygen sensor element is held at the front end of the metallic terminal by a pressing force acting toward the axis of the solid electrolyte. Namely, a plurality of pressing forces acting from the outer periphery of the solid electrolyte toward the axis of the solid electrolyte can be adequately balanced. The solid electrolyte can be held stably by the front ends of the metallic terminals.

Yet further, it is preferable that a cross section of the solid electrolyte (11) is circular at a portion where the front ends of the first and second metallic terminals (27, 26) are resiliently brought into contact with the first and second leads (24, 22; 240, 220), respectively, or at a portion where the front ends of the third metallic terminals (28, 29) are resiliently brought into contact with the electric heater (35). With this arrangement, the pressing portions are symmetrically located. The solid electrolyte can be easily held by the metallic terminals.

Moreover, it is preferable that the front ends of the metallic terminals applying the pressing force toward the axis of the solid electrolyte are rotation symmetric along a circle surrounding the axis of the solid electrolyte. With this arrangement, the pressing forces of the front ends of the metallic terminals acting toward the axis of the solid electrolyte can be balanced. The solid electrolyte or the oxygen sensor element is not subjected to a bending stress or an angular moment. For example, when a total of four pressing portions are provided at the front ends of the metallic terminals, these pressing portions are equally spaced at the same angular intervals of 90 degrees to realize a rotation symmetric arrangement.

According to another aspect of the present invention, an oxygen sensor comprises a cup-shaped solid electrolyte (11) having an opening at a base end side and a bottom at a front end side. A measuring electrode (23) is provided on an outer surface of the front end side of the solid electrolyte. A reference electrode (21) is provided on an inner surface of the front end side of the solid electrolyte. A first lead (24; 240) is brought into electrical contact with the measuring electrode and extends to the base end side of the solid electrolyte. A second lead (22; 220) is brought into electrical contact with the reference electrode and extends to the base end side of the solid electrolyte. A housing (41) has a through hole for accommodating the solid electrolyte. A base body (45) is fixed to the housing and covers the base end side of the solid electrolyte. A first metallic terminal (27) is brought into electrical contact with the first lead and extends to a base end of the base body. A second metallic terminal (26) is brought into electrical contact with the second lead and extends to the base end of the base body. And, a relay plate (32) is interposed between the first metallic terminal and the first lead to electrically connect the first metallic terminal to the first lead. The relay plate is made of a leaf spring so that the relay plate presses the first lead by a resilient force caused by a springback of the leaf spring.

FIG. 11 schematically shows an engagement between the relay plate and the first lead in accordance with the present invention. As shown in FIG. 11, a signal output portion 51 of the first lead is formed into an arc shape fitting to an outer surface of the cylindrical solid electrolyte. A relay plate 52 is a leaf spring causing a resilient force by its springback reaction. The relay plate 52 presses the signal output portion 51 toward the axis of the solid electrolyte as indicated by an arrow Y in the drawing. Thus, the connection between the signal output portion 51 and the relay plate 52 can be surely maintained. Furthermore, a dislocation may be caused between the signal output portion 51 and the relay plate 52 as indicated by a dotted line in the drawing. Even in such a condition, the signal output portion 51 can be connected with the relay plate 52 without causing any imperfect contact. When the contacting portion of the relay plate 52 is completely flat, there is no possibility that the contact point is dislocated.

An area where the signal output portion is brought into contact with the relay plate can be narrowed. Accordingly, numerous relay plates and base ends of the primary leads can be provided along the outer cylindrical surface of the solid electrolyte. There is no necessity of processing the connecting portion between the primary lead and the relay plate into a multistage configuration. The length of the solid electrolyte can be shortened.

A plurality of relay plates can be disposed in a rotation symmetric arrangement along the same circle surrounding the axis of the oxygen sensor. With this arrangement, the pressing forces of the relay plates acting toward the axis of the solid electrolyte can be balanced. The solid electrolyte is not subjected to a bending stress or an angular moment. For example, a total of four relay plates may be provided. The leads of internal and external electrodes are connected with these relay plates at different four portions. The relay plates are spaced equally at regular intervals of 90 degrees, realizing a rotation symmetric arrangement.

According to the above-described arrangement of the present invention, as understood from FIGS. 1 and 6 later described, the relay arrangement for transmitting electric signals of the oxygen sensor can be greatly simplified.

According to the features of the preferred embodiments of the present invention, it is preferable that the second lead (22; 220) is exposed on an outer surface at the base end side of the solid electrolyte. And, a relay plate (31) is interposed between the second metallic terminal (26) and the second lead (22; 220) to electrically connect the second metallic terminal to the second lead. The relay plate (31) is made of a leaf spring so that the relay plate presses the second lead by a resilient force caused by a springback of the leaf spring. With this arrangement, an electric conductance between the second lead and the second metallic terminal can be adequately maintained.

Furthermore, it is preferable that an electric heater (35) is located on an outer surface of the solid electrolyte. Third metallic terminals (28, 29) are brought into electrical contact with the electric heater and extend to the base end of the base body. And, relay plates (33, 34) are interposed between the third metallic terminals and the electric heater to electrically connect the third metallic terminals to the electric heater. The relay plates (33, 34) are made of a leaf spring so that the relay plate (33, 34) press the electric heater (35) by a resilient force caused by a springback of the leaf spring.

With the above-described arrangement, the internal and external electrodes of the solid electrolyte and the electric heater can be connected via, for example, a total of four relay plates. As a result, the relay plates can be disposed in a rotation symmetric arrangement at the same angular intervals of 90 degrees even when each relay plate is connected to a corresponding lead or the electric heater at one point. Thus, the rotation symmetric arrangement of the relay plates can be realized along the same circle surrounding the axis of the oxygen sensor (refer to FIG. 3B).

With the above-described arrangement, the base ends of the first lead and the electric heater are connected to the metallic terminals at, for example, three portions via the above-described relay plates.

Accordingly, a total of three relay plates are provided at three connecting points. The relay plates are equally spaced at the same angular intervals of 120 degrees so as to realize a rotation symmetric arrangement, even when each relay plate is connected to a corresponding lead at one point. Accordingly, the rotation symmetric arrangement of the relay plates can be realized along the same circle surrounding the axis of the oxygen sensor (refer to FIG. 8).

BRIEF DESCRIPTION OF THE DRAWINGS

The above and other objects, features and advantages of the present invention will become more apparent from the following detailed description which is to be read in conjunction with the accompanying drawings, in which.

DESCRIPTION OF THE PREFERRED EMBODIMENTS

Figure 1:
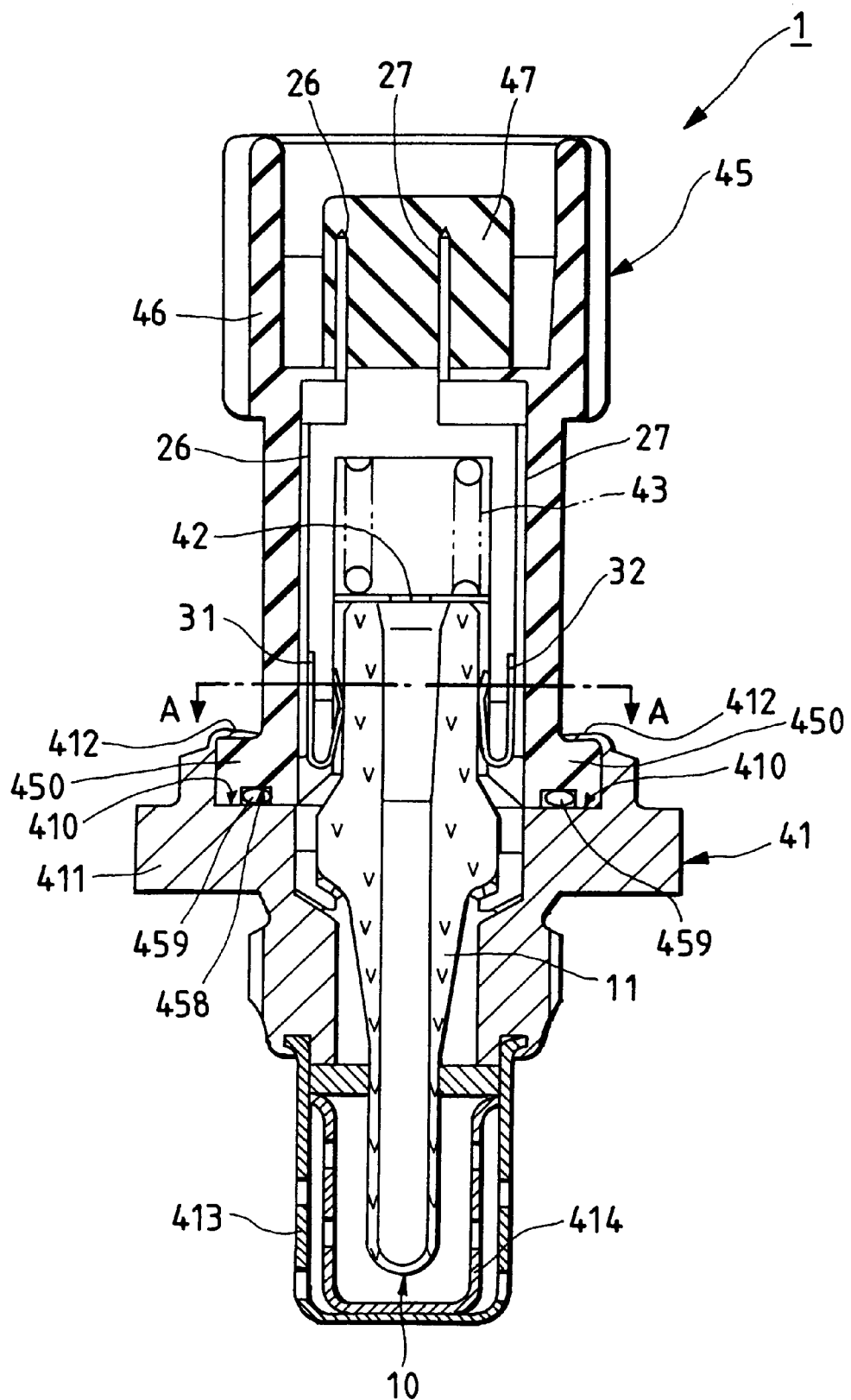
FIG. 1 is a cross-sectional view showing an oxygen sensor in accordance with a first embodiment of the present invention, taken along a line X—X of FIG. 3A.

Preferred embodiments of the present invention will be explained hereinafter with reference to accompanied drawings. Identical parts are denoted by the same reference numerals throughout the drawings.

First Embodiment

An oxygen sensor in accordance with a first embodiment of the present invention will be explained with reference to FIGS. 1 to 5. As shown in FIG. 1, an oxygen sensor 1 of the first embodiment comprises a housing 41. An oxygen sensor element 10 is inserted in a through hole of the housing 41 and fixed to the housing 41. A base body 45 is provided at an upper end of the housing 41. The base body 45 is made of a resin.

The base body 45 has a flange 450 at a lower end (or front end). The housing 41 has a caulking portion 410 at an upper end (or base end). The caulking portion 410 is deformable by a pressing force acting toward the axis of the oxygen sensor 1. The flange 450 is fixed to the housing 41 by the deformed caulking portion 410. An O ring 459 is interposed between the flange 450 and the caulking portion 410.

As shown in FIG. 1, the oxygen sensor 1 of the first embodiment comprises an oxygen sensor element 10. This oxygen sensor element 10 comprises a cup-shaped solid electrolyte 11 which conducts oxygen ions. Element protecting covers 413 and 414, configured in a double layered structure, cooperatively cover a bottom part of the oxygen sensor element 10. A plurality of gas holes are opened on the walls of the element protecting covers 413 and 414. The upper ends of the element protecting covers 413 and 414 are fixed to the housing 41. The inside space of the housing 41 accommodates the front or lower part of the oxygen sensor element 10. The base body 45 has an inside space for accommodating the base end of the oxygen sensor element 10.

Figure 4A:
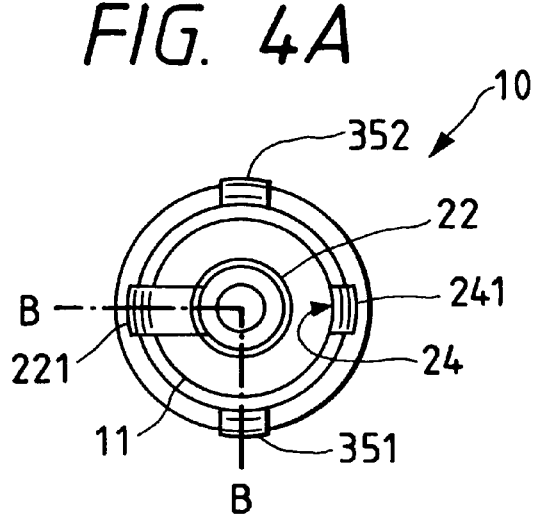
FIG. 4A is a plane view showing the oxygen sensor of the first embodiment.
Figure 4B:
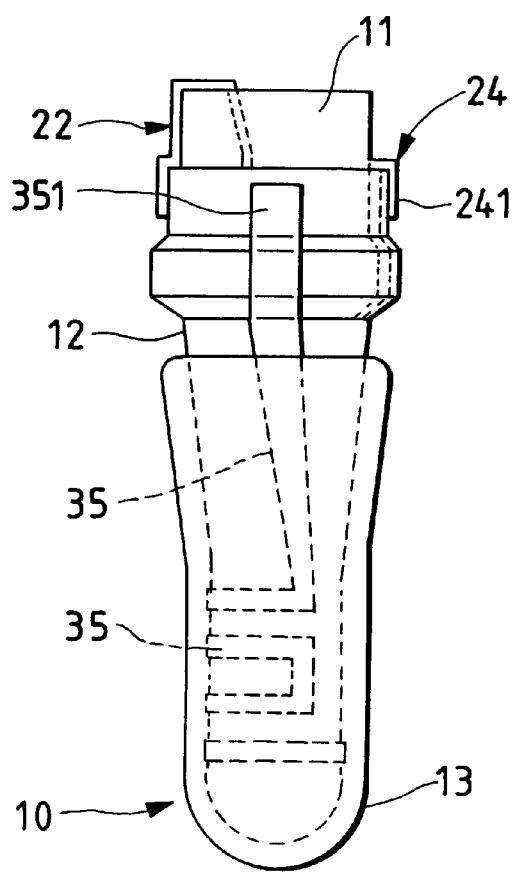
FIG. 4B is a front view showing the oxygen sensor of the first embodiment.
Figure 4C:
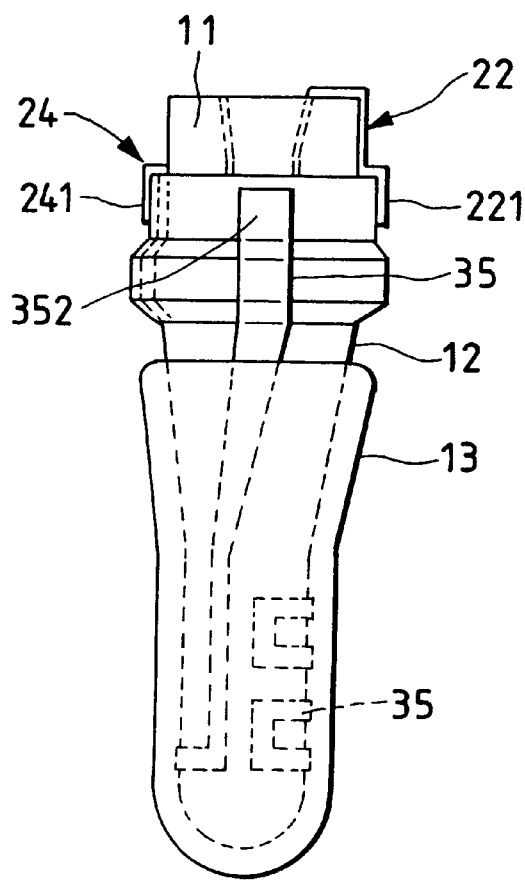
FIG. 4C is a reverse view showing the oxygen sensor of the first embodiment.
Figure 5:
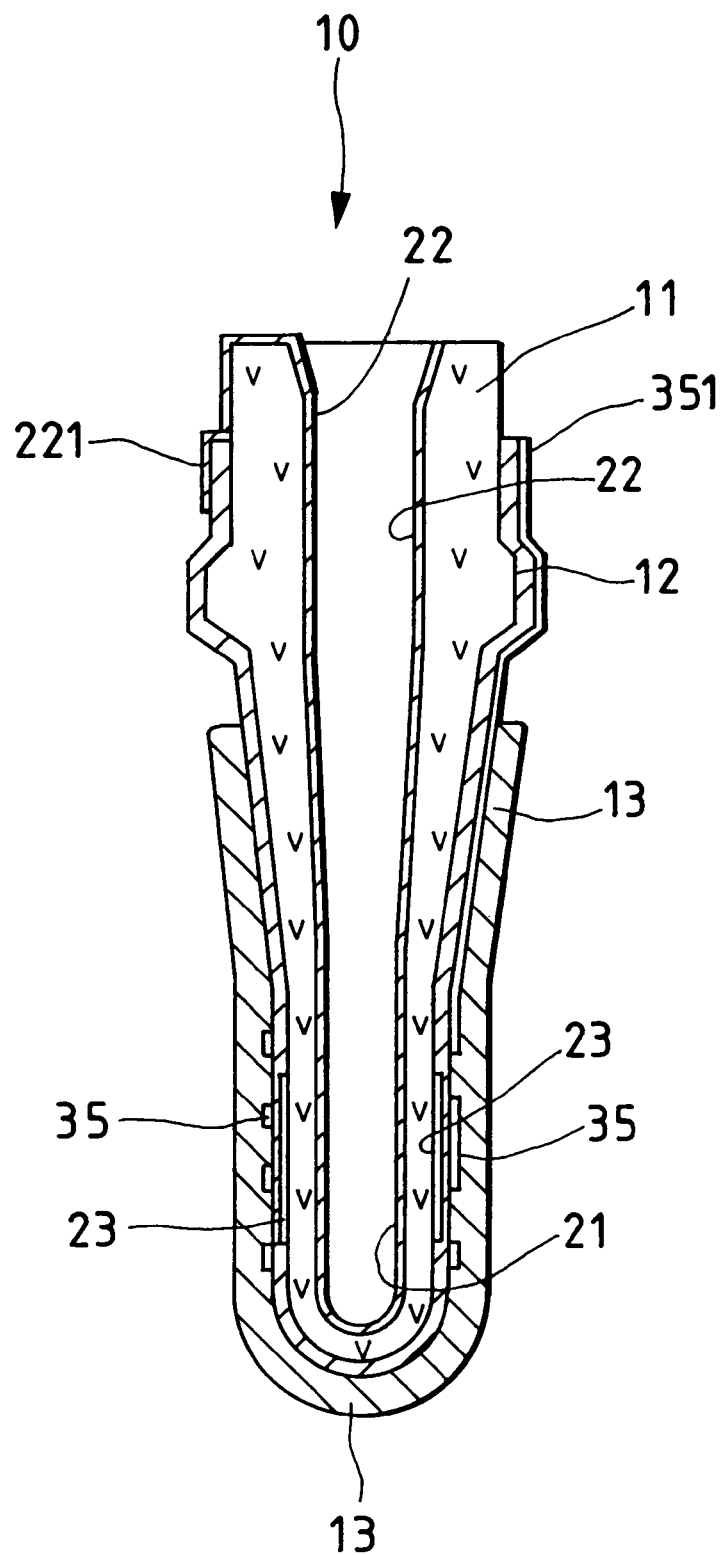
FIG. 5 is a cross-sectional view showing the oxygen sensor of the first embodiment, taken along a line B—B of FIG. 4A.

As shown in FIG. 5, a reference electrode 21 and a second lead 22 are provided on an inside surface of the solid electrolyte 11 of the oxygen sensor element 10. A measuring electrode 23 and a first lead 24 are provided on an outside surface of the solid electrolyte 11. As shown in FIGS. 4A to 4C, the first lead 24 and the second lead 22 have signal output portions 241 and 221, respectively. These signal output portions 241 and 221 are positioned on the outer surface of the solid electrolyte 11.

Figure 3A:
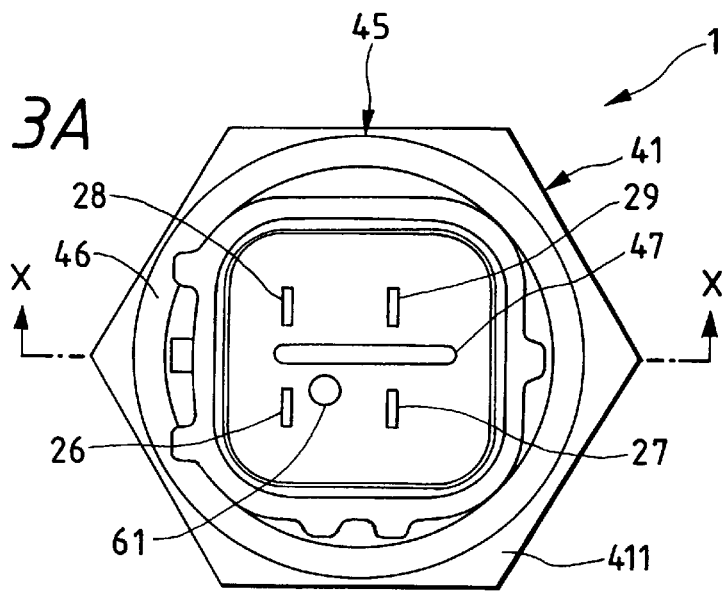
FIG. 3A is a plane view showing the oxygen sensor of the first embodiment.
Figure 3B:
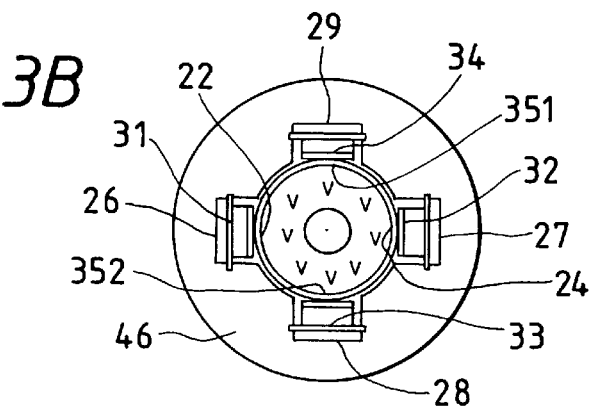
FIG. 3B is a cross-sectional view showing the oxygen sensor of the first embodiment taken along a line A—A of FIG. 1.

On the other hand, the base body 45 is provided with gas holes (not shown) which introduce reference gas (e.g., air) inside the oxygen sensor element 10. As shown in FIGS. 1, 3A and 3B, a first metallic terminal 27 and a second metallic terminal 26 are integrally molded in the base body 45. The first metallic terminal 27 and the second metallic terminal 26 transmit electric signals to an external device, such as an engine control unit. Relay plates 31 and 32 are provided between the front end of the base body 45 and the base end of the oxygen sensor element 10. The relay plate 31 electrically connects the second metallic terminal 26 with the second lead 22. The relay plate 32 electrically connects the first metallic terminal 27 with the first lead 24. The relay plates 31 and 32 are made of leaf springs, each producing a resilient force by a springback. The relay plate 31 presses a signal output portion 221 (refer to FIG. 4A) of the second lead 22. The relay plate 32 presses a signal output portion 241 (refer to FIG. 4A) of the first lead 24.

Furthermore, as shown in FIGS. 4B and 4C, an electric heater 35 is provided on the outer surface of the solid electrolyte 11 of the oxygen sensor element 10. The electric heater 35 is provided at a predetermined position where the electric heater 35 does not interfere with the measuring electrode 23 and the first lead 24. The electric heater 35 has power supply terminals 351 and 352 at the base end side of the oxygen sensor element 10. A pair of third metallic terminals 28 and 29 (refer to FIGS. 3A and 3B) is provided for the electric heater 35. A pair of relay plates 33 and 34 is provided for the electric heater 35, too. The relay plate 33 connects the power supply terminal 352 and the third metallic terminal 28. The relay plate 34 connects the power supply terminal 351 and the third metallic terminal 29 (refer to FIG. 3B). The relay plates 31 to 34 are positioned along the same circle surrounding the axis of the solid electrolyte 11 at the same angular intervals to realize a rotation symmetric arrangement.

Figure 2:
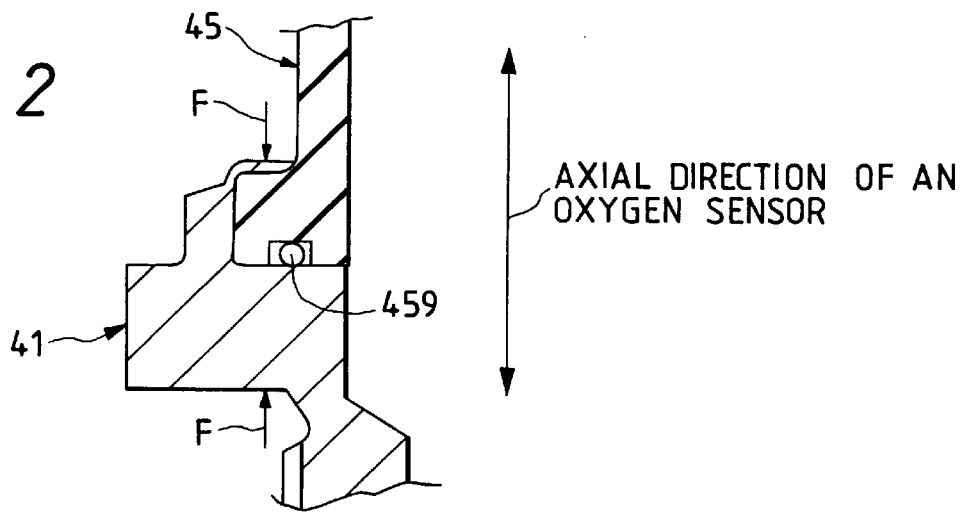
FIG. 2 is an enlarged cross-sectional view showing a fixed condition of the oxygen sensor where a housing and a base body are fixed by caulking.

Hereinafter, supplemental explanations are given for the above-described components. As shown in FIGS. 1 and 2, the housing 41 has a flange 411. The oxygen sensor 1 is fixedly mounted on a wall of an exhaust passage pipe via this flange 411. The caulking portion 410 is provided at an upper end of the flange 411. The caulking portion 410 is deformable. The base body 45 is fixed to the housing 41 by the deformed caulking portion 410. More specifically, the flange 450 of the base body 45 is placed face to face on the caulking portion 410. A base end 412 of the caulking portion 410 is deformed inward. The housing 41 is fixed with the base body 45 by the deformed base end 412. In this caulking operation, a pressing force F indicated in FIG. 2 is applied to the flange 450 from above, while the same pressing force F is applied to the housing 41 from below. The pressing force F acts in a direction parallel to the axis of the oxygen sensor element.

The O ring 459 is interposed between the flange 450 and the caulking portion 410. The flange 450 has an annular groove 458 in which the O ring 459 is disposed. Then, the element protecting covers 413 and 414 are attached to the lower end (i.e., front end) of the housing 41. The protecting covers 413 and 414 are inserted in the exhaust passage pipe and exposed to the exhaust gas flowing in the exhaust passage pipe.

The oxygen sensor element 10 is placed in position in the housing 41. A spring 43 resiliently urges the base end of the oxygen sensor element 10 via a sheet 42. Thus, the oxygen sensor element 10 is pushed downward (i.e., toward the front end thereof). The base body 45 includes a resin body 46 at an inside thereof. The first metallic terminal 27, the second metallic terminal 26 and the third metallic terminals 28 and 29 are molded in the resin body 46. The base body 45 including the resin body 46 is preferably made of polyphenylene sulfide. In FIG. 1, reference numeral 47 represents a retainer. An atmospheric hole 61 is provided at an end of the base body 45, as shown in FIG. 3A. The atmospheric hole 61 introduces air inside the base body 45.

The oxygen sensor element 10, as shown in FIGS. 4A–4C and 5, comprises the solid electrolyte 11, the reference electrode 21, the measuring electrode 23 and the electric heater 35 as described above. Furthermore, the oxygen sensor element 10 comprises an anti-diffusion layer 12 interposed between the measuring electrode 23 and the electric heater 35. The anti-diffusion layer 12 has a function of insulating the measuring electrode 23 from the electric heater 35. Another anti-diffusion layer 13, made of magnesia spinel, covers the surface of the electric heater 35. The electric heater 35 quickly and uniformly increases the temperature of a portion of the solid electrolyte 11 located near the electrodes 21 and 23. As shown in FIGS. 4B and 4C, the electric heater 35 is arranged in a zigzag fashion along the outside surface of the solid electrolyte 11.

The front ends of the first, second and third metallic terminal 27, 26 and 28, 29 are configured into a flat plate as shown in FIG. 3B, or a wire or a curved plate convex to a direction normal to an axis of said oxygen sensor.

Next, operations and effects of the oxygen sensor in accordance with the first embodiment will be explained hereinafter. The oxygen sensor of the first embodiment has the base body 45 made of a resin. In general, the resin is easy to process or machine. The base body 45 can be flexibly fabricated into a desirable configuration. Furthermore, the base body 45 can be manufactured as a single component, not a combination of a plurality of members. Accordingly, the base body 45 of the first embodiment of the present invention is easy to install when it is installed on the housing 41, compared with the conventional base body which is based on the combination of the plural members.

As described above, according to the first embodiment of the present invention, it becomes possible to provides an oxygen sensor having a base body easy to manufacture and easy to install.

Furthermore, according to the oxygen sensor element 10 of the first embodiment, the base body 45 is fixed to the housing 41 by caulking. A pressing force is applied to the caulking portion 410 of the housing 41 in a direction parallel to the axis of the oxygen sensor 1. Thus, the flange 450 of the base body 45 is firmly and tightly fixed to the housing 41 by the caulking portion 410 of the housing 41 deformed in this manner. Accordingly, the caulking operation can be performed easily, while an excellent sealing ability is maintained between the metallic housing 41 and the resin base body 45. Furthermore, providing the O ring 459 between the base body 45 and the housing 41 is effective to improve the sealing ability. Thus, it becomes possible to prevent any moisture component existing outside the oxygen sensor 1 from entering inside the oxygen sensor 1.

Figure 11:
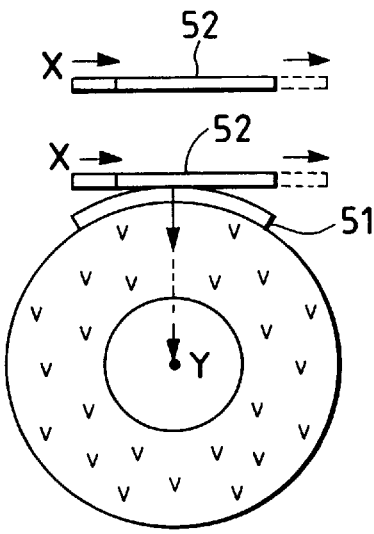
FIG. 11 is a view schematically illustrating an engagement between a relay plate and a first lead in accordance with the present invention.

As shown in FIGS. 4A to 4C, the signal output portion 221 of the first lead 24, the signal output portion 241 of the second lead 22 and two base ends 351, 352 of the electric heater 35 are respectively configured into an arc shape, fitting to the cylindrical outer surface of the base end portion of the solid electrolyte 11. As shown in FIG. 1, the relay plates 31 to 34 are respectively made of a leaf spring causing a resilient force by a springback. Thus, the members 221, 241, 351 and 352 can be surely brought into contact with the relay plates 31 to 34. Even if any dislocation is caused between the members 221, 241, 351, 352 and the relay plates 31 to 34, their contact points can be steadily maintained and no imperfect contact is caused. Thus, the element is not subjected to an angular moment about the axis of the element (as explained referring to FIG. 11).

Even when the members 221, 241, 351, 352 are brought into contact with the relay plates 31 to 34 at smaller contact areas, there is no possibility of causing an imperfect contact. Accordingly, numerous relay plates 31–34 and the signal output portions 221, 241 of the leads or the base ends 351, 352 of the electric heater 35 can be provided along the same outer surface of the cylindrical solid electrolyte 11. Thus, the axial length of the solid electrolyte 11 can be shortened.

The four relay plates 31 to 34 are positioned in a rotation symmetric arrangement along the same circle surrounding the axis of the solid electrolyte 11. The pressing forces of these relay plates 31 to 34 can be balanced and uniformly applied to the solid electrolyte 11. Thus, the solid electrolyte 11 is not subjected to a bending stress or an angular moment. Furthermore, as understood from the above-explained drawings, the relay arrangement for transmitting electric signals of the oxygen sensor 1 can be greatly simplified, compared with the conventional arrangement.

The measuring electrode 23 is integral with the first lead 24. The reference electrode 21 is integral with the second lead 22.

As apparent from the foregoing description, according to the first embodiment of the present invention, it becomes possible to provide an oxygen sensor 1 having a simplified arrangement and capable of surely transmitting electric signals.

Second Embodiment

An oxygen sensor of a second embodiment of the present invention comprises a different oxygen sensor element. A measuring electrode is provided on the oxygen sensor element and connected to a first metallic terminal via a relay plate. A reference electrode is provided on the oxygen sensor element and is connected directly to a second metallic terminal without using a relay plate. More specifically, as shown in FIG. 10, an oxygen sensor element 10 has a solid electrolyte 11. A reference electrode 21 and a second lead 220 are provided on an inside surface of the solid electrolyte 11. A measuring electrode 23, a first lead 240 (refer to FIG. 9) and an electric heater 35 are provided on an outside surface of the solid electrolyte 11.

Figure 6:
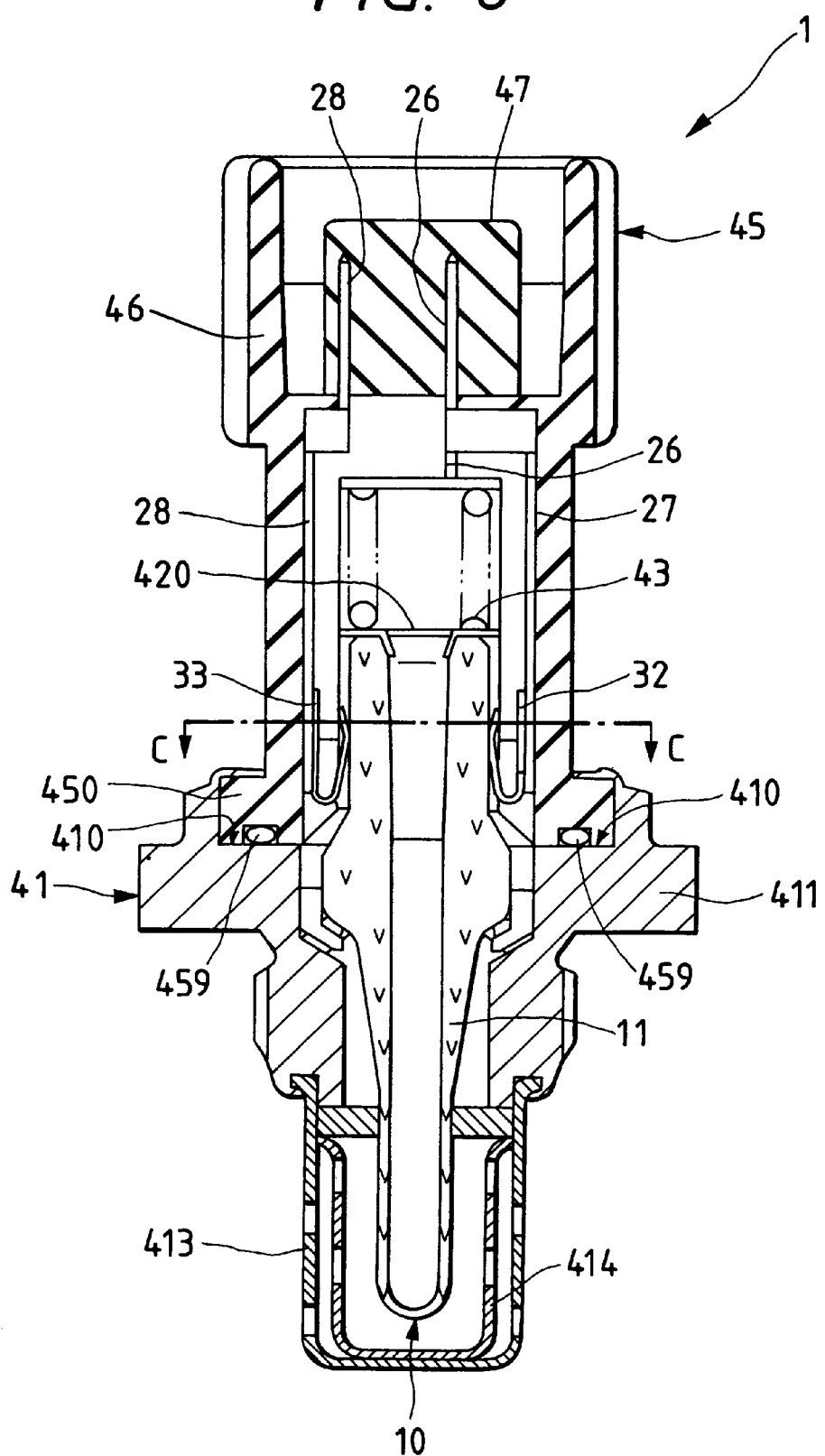
FIG. 6 is a cross-sectional view showing an oxygen sensor in accordance with a second embodiment of the present invention, taken along a line D—D of FIG. 8.
Figure 7:
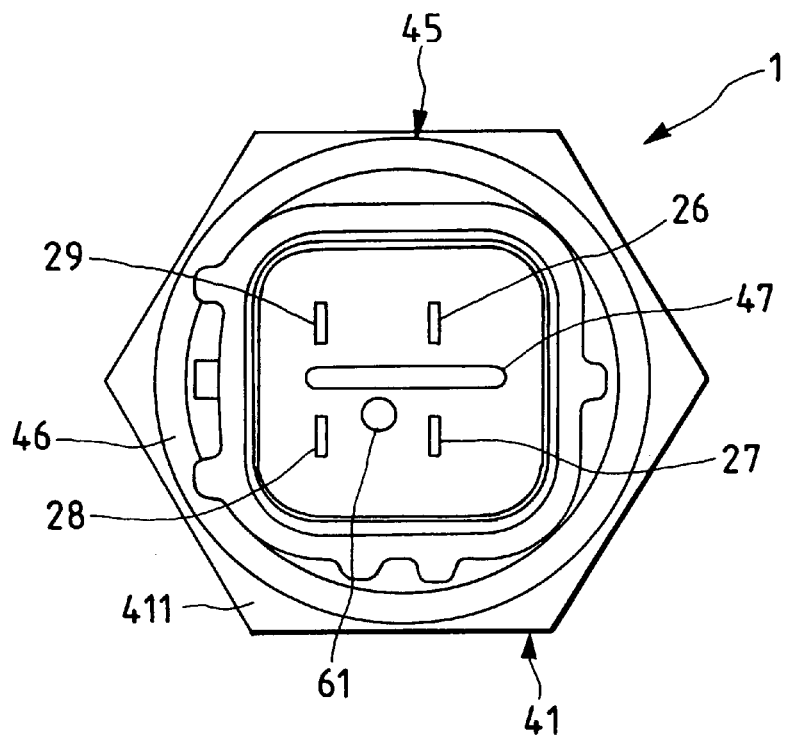
FIG. 7 is a plan view showing the oxygen sensor of the second embodiment.
Figure 9:
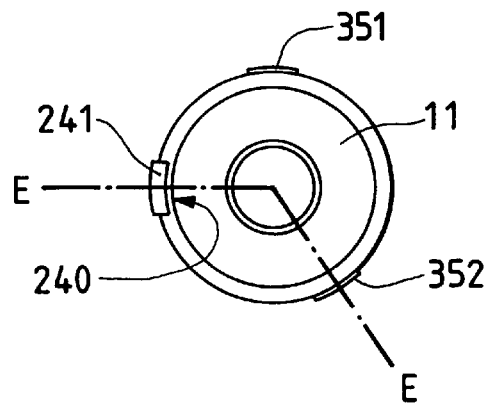
FIG. 9 is a plan view showing an oxygen sensor element of the second embodiment.
Figure 10:
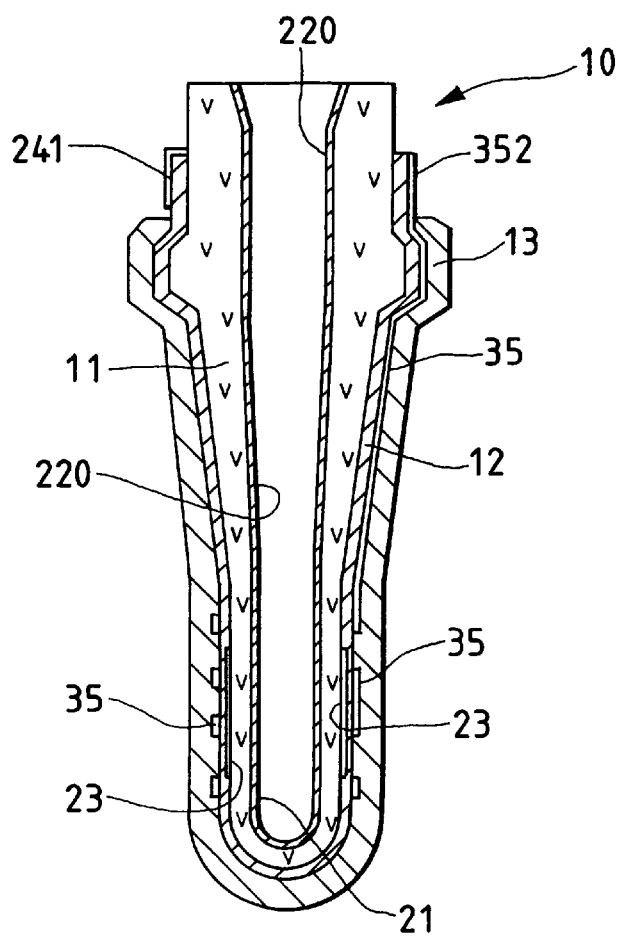
FIG. 10 is a cross-sectional view showing the oxygen sensor element of the second embodiment, taken along a line E—E of FIG. 9.

As shown in FIG. 9, a base end 241 of the first lead 240 of the measuring electrode 23 and base ends 351, 352 of the electric heater 35 are exposed on an outer surface at the base end portion of the solid electrolyte 11. Furthermore, as shown in FIGS. 6 and 7, a first metallic terminal 27, a second metallic terminal 26 and third metallic terminals 28 and 29 are molded in a base body 45. The second metallic terminal 26 connects the reference electrode 21 to an external device, such as an engine control unit, to transmit sensor signals. The first metallic terminal 27 connects the measuring electrode 23 to the external device. The third metallic terminals 28 and 29 connect the electric heater 35 to an electric power source.

Figure 8:
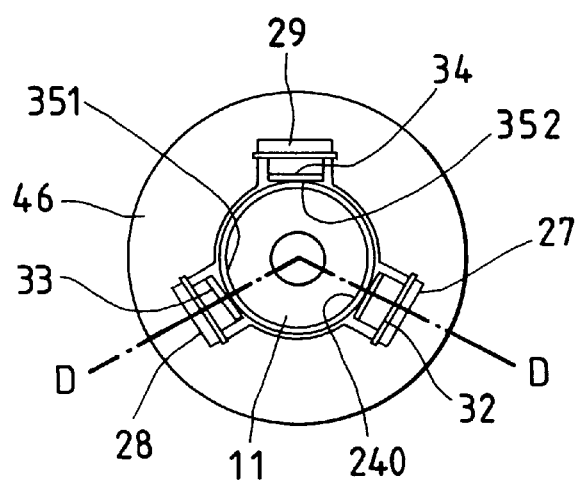
FIG. 8 is a cross-sectional view showing the oxygen sensor of the second embodiment, taken along a line C—C of FIG. 6.

A plurality of relay plates 32 to 34 are provided between the front end of the base body 45 and the base end of the oxygen sensor element 10, as shown in FIGS. 8 and 9. The relay plate 32 connects the first lead 240 of the measuring electrode 23 to the first metallic terminal 27. The relay plates 33 and 34 connect the base ends 351 and 352 of the electric heater 35 to the third metallic terminals 28 and 29, respectively. On the other hand, the second lead 220 of the reference electrode 21, provided on the inside surface of the solid electrolyte 11 (refer to FIG. 10), is electrically connected to the second metallic terminal 26 via a conductive sheet 420 and a spring 43, as shown in FIG. 6. The rest of the structural arrangement is identical with that of the first embodiment.

As shown in FIG. 8, the three relay plates 32 to 34 are equally spaced at the same angular intervals of 120 degrees along the same circle surrounding the axis of the solid electrolyte 11, realizing a rotation symmetric arrangement. According to the oxygen sensor of the second embodiment, the pressing forces of the relay plates 32 to 34 are balanced with respect to the solid electrolyte 11. Accordingly, in the oxygen sensor 1 of the second embodiment, the solid electrolyte 11 is not subjected to a bending stress or an angular moment. The rest of the operations and effects is identical with those of the first embodiment.

Third Embodiment

An oxygen sensor of a third embodiment is substantially identical with those disclosed in the first and second embodiments except that the relay plates 31 to 34 are integrally formed with the metallic terminals 26 to 29 respectively, although not shown in the drawings. The reference electrode 21 is integral with the second lead 22 or 220.

According to the third embodiment, the metallic terminals are not formed separately from the relay plates. The rest of the structural arrangement of the third embodiment is identical with those disclosed in the first or second embodiment.

Fourth Embodiment

Figure 13:
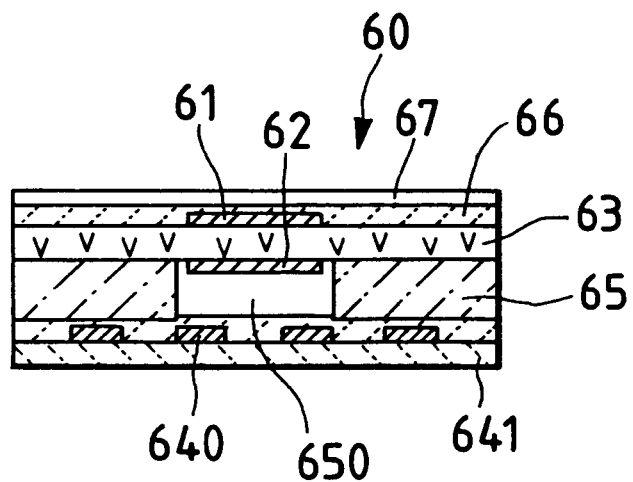
FIG. 13 is a cross-sectional view showing an oxygen sensor element of the fourth embodiment.

A fourth embodiment of the present invention provides an oxygen sensor having a laminated oxygen sensor element. As shown in FIG. 13, a laminated oxygen sensor element 60 of the fourth embodiment comprises a substrate 63 made of a solid electrolyte. A measuring electrode 61 is formed on a surface of the substrate 63. A reference electrode 62 is formed on an opposed surface of the substrate 63. A reference chamber 650 is formed in an insulating substrate 65. The reference chamber 650 faces the reference electrode 62. An electric heater 640 is provided on a lower surface of the substrate 65. The electric heater 640 is mounted on a substrate 641. The measuring electrode 61 has an upper surface covered by an anti-diffusion layer 66. An upper surface of the anti-diffusion layer 66 is covered by a trapping layer 67 which traps poisonous substances.

Figure 12:
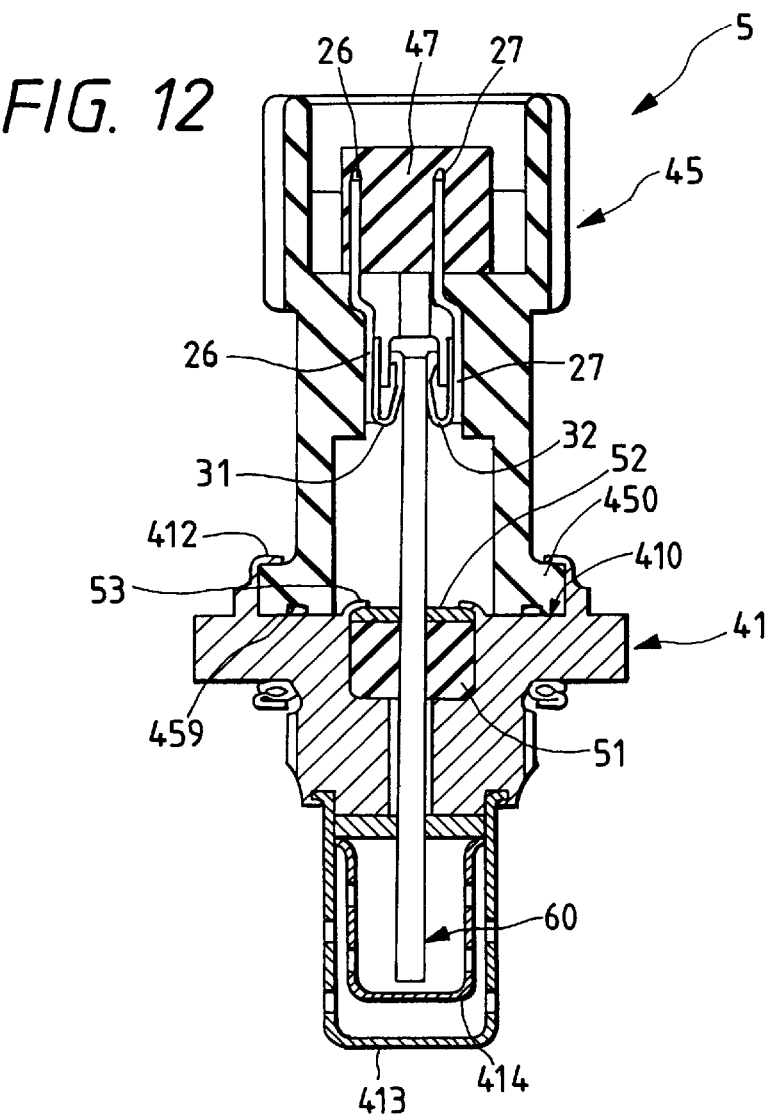
FIG. 12 is a cross-sectional view showing an oxygen sensor in accordance with a fourth embodiment of the present invention.

As shown in FIG. 12, the oxygen sensor 5 of the fourth embodiment comprises a housing 41. The laminated oxygen sensor element 60 is inserted and fixed in this housing 41. A resin base body 45 is provided at an upper end of the housing 41.

The oxygen sensor element 60 is provided with first and second leads (not shown). The oxygen sensor 5 comprises a first metallic terminal 27 electrically connected to the first lead and a second metallic terminal 26 electrically connected to the second lead. The first metallic terminal 27 is connected to the first lead via a relay plate 32. The second metallic terminal 26 is connected to the second lead via a relay plate 31. Both the first metallic terminal 27 and the second metallic terminal 26 are insert molded in a resin body 47 provided inside the base body 45.

The oxygen sensor element 60 of the oxygen sensor 5 is installed in the following manner. First, a rubber packing 51 is prepared. This rubber packing 51 has an insertion hole into which the oxygen sensor element 60 is inserted. The rubber packing 51 has a shape or size slightly larger that the shape or size of an inner bore of the housing 41. The oxygen sensor element 60 is inserted in the above-described insertion hole. Thereafter, the rubber packing 51 is press fitted into the housing 41. The outer diameter of the rubber packing 51 is reduced due to the compression of the press-fitted rubber packing 51. The inner diameter of the insertion hole is reduced slightly. With this compression of the rubber packing 51, the oxygen sensor element 60 is firmly held in the insertion hole. Next, a metallic ring 52 is placed on the upper surface of the rubber packing 51.

Figure 14:
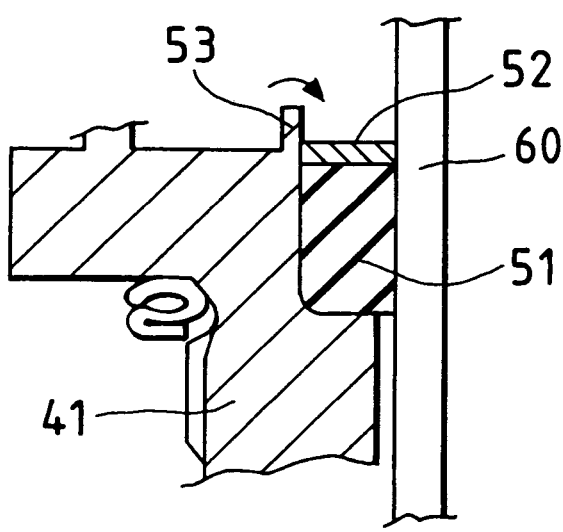
FIG. 14 is an enlarged cross-sectional view showing a caulking portion and a housing in accordance with the fourth embodiment.
Figure 15:
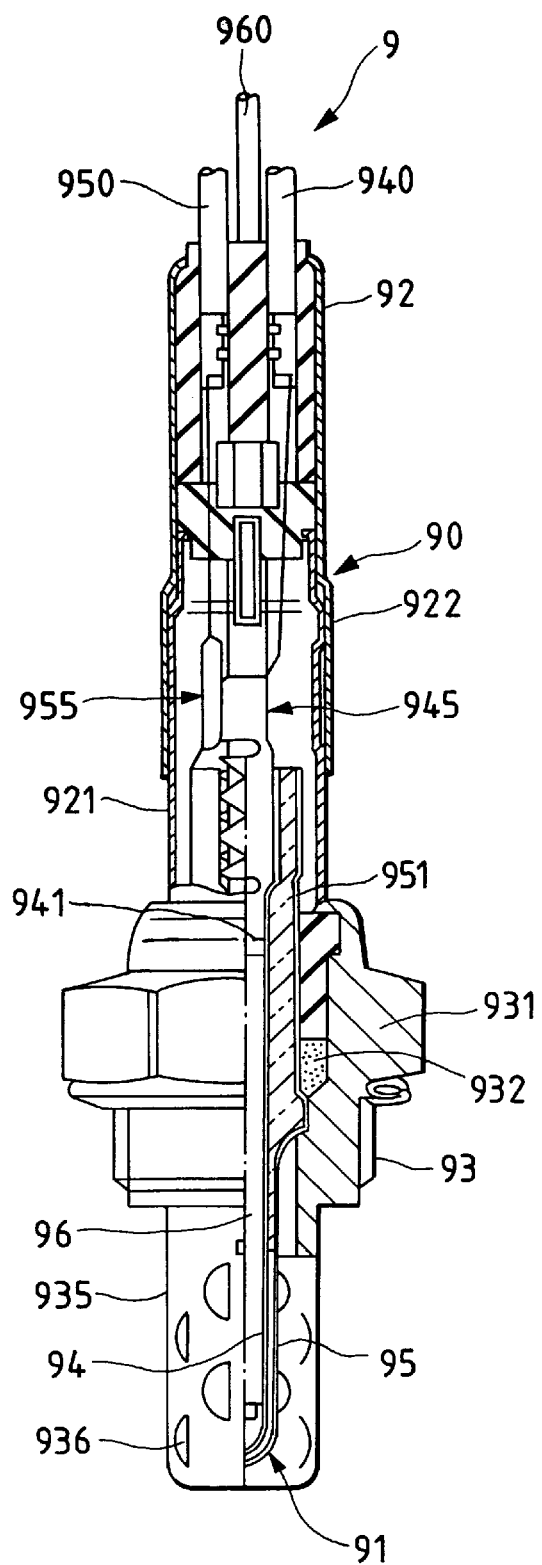
FIG. 15 is a partial cross-sectional front view showing a conventional oxygen sensor.

As understood from FIG. 14, a caulking portion 53 is formed at the upper end of the housing 41. After the metallic ring 52 is disposed on the rubber packing 51, the caulking portion 53 is deformed inward by a pressing force applied in a direction shown by an arrow (i.e., toward the axis of the oxygen sensor) as shown in FIG. 14. Thus, the metallic ring 52 is fixed by the deformed caulking portion 53. With this arrangement, the rubber packing 51 is caulked by the pressing force acting toward the axis of the oxygen sensor 5. The rubber packing 51 is thus firmly fixed to the housing 41. Thereafter, the base body 45 is tightly connected to the housing 41 by caulking in the same manner as in the first embodiment. The metallic terminals 26 and 27 are insert molded and fixed in the resin body 47. In this manner, the oxygen sensor 5 of the fourth embodiment is obtained. The rest of the arrangement is identical with that of the first embodiment.

According to the oxygen sensor of the fourth embodiment, it becomes possible to obtain an oxygen sensor having a base body easy to manufacture and easy to install. Substantially the same effects as those of the first embodiment can be obtained in this embodiment.

This invention may be embodied in several forms without departing from the spirit of essential characteristics thereof. The present embodiments as described are therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

What is claimed is:

1. A gas sensor comprising:
    a housing;
    a gas sensor element inserted and fixed in said housing, said gas sensor having one end exposed to a measuring gas and a second end exposed to air;
    a resin material base body fixed directly to said housing and covering said second end of said gas sensor; and
    at least two metallic terminals, connected to said gas sensor element, used for outputting a sensor signal detected by said gas sensor, said at least two metallic terminals being insert molded together with said base body.

2. The gas sensor in accordance with claim 1, wherein said base body has a flange at a longitudinal end facing to said housing, and said housing has a caulking portion on a longitudinal end surface facing to said base body, said caulking portion has a deformable portion at a radial outer portion, said deformable portion is deformed when a pressing force is applied thereon, so that said flange of said base body is fastened between the end surface of said housing and said deformable portion of the caulking portion when the pressing force is applied in a longitudinal direction of said gas sensor.

3. The gas sensor in accordance with claim 2, wherein an O ring is interposed between said flange and said caulking portion.

4. The gas sensor in accordance with claim 1, wherein
    said gas sensor element comprises a solid electrolyte, a measuring electrode provided on an outer surface of a front end side of said solid electrolyte, and a first lead electrically conductive with said measuring electrode,
    said first lead of said gas sensor element is connected via a relay plate to one of said at least two metallic terminals used for outputting said sensor signal detected by said gas sensor, and
    said relay plate is brought into contact with said one of said at least two metallic terminals by a pressing force acting in a direction normal to a longitudinal axis of said gas sensor.

5. The gas sensor in accordance with claim 1, wherein said gas sensor element is configured into a cup shape.

6. The gas sensor in accordance with claim 1, wherein said gas sensor element is a laminated element.

7. The gas sensor in accordance with claim 1, wherein
    said gas sensor element is a laminated element, and a deformable portion is integrally formed at a radial inner end of said housing, and
    said deformable portion is deformed by a pressing force applied thereon so as to securely fix said gas sensor element to said housing via a cushioning member intervening between the housing and said gas sensor element.

8. The gas sensor in accordance with claim 1, wherein a front end of one of said at least two metallic terminals is equipped with an urging member configured into a flat plate, a wire, or a curved plate convex to a direction normal to a longitudinal axis of said gas sensor.

9. A gas sensor comprising:
    a gas sensor element comprising a cup-shaped solid electrolyte having an opening at a base end side and a bottom at a front end side, said base end side being exposed to the air and said front end side being exposed to a measuring gas;
    a measuring electrode provided on an outer surface of the front end side of said solid electrolyte;
    a reference electrode provided on an inner surface of said front end side of said solid electrolyte;
    a first lead brought into electrical contact with said measuring electrode and extending to said base end side of said solid electrolyte;
    a second lead brought into electrical contact with said reference electrode and extending to said base end side of said solid electrolyte;
    a housing for accommodating said solid electrolyte;
    a base body fixed directly to said housing and covering the base end side of said solid electrolyte;
    a first metallic terminal brought into electrical contact with said first lead and extending to a base end of said base body; and
    a second metallic terminal brought into electrical contact with said second lead and extending to the base end of said base body,
    wherein said base body is made of a resin,
    said first metallic terminal is insert molded together with said resin base body,
    a front end of said first metallic terminal is equipped with an urging member configured into a flat plate, a wire, or a curved plate convex to a longitudinal axis of said solid electrolyte, and
    said urging member equipped at front end of said first metallic terminal causes a pressing force acting toward said first lead in a direction which is substantially normal to the longitudinal axis of said solid electrolyte so that said front end of said first metallic terminal is brought into contact with said first lead.

10. The gas sensor in accordance with claim 9, wherein
    said second lead is exposed on an outer surface at the base end side of said solid electrolyte,
    a front end of said second metallic terminal is equipped with an urging member configured into a flat plate, a wire, or a curved plate convex to the longitudinal axis of said solid electrolyte, and said urging member equipped at said front end of said second metallic terminal causes a pressing force acting toward said second lead in a direction which is substantially normal to the longitudinal axis of said solid electrolyte so that said front end of said second metallic terminal is brought into contact with said second lead.

11. The gas sensor in accordance with claim 9, wherein an electric heater is located on an outer surface of aid solid electrolyte, a third metallic terminal is brought into electrical contact with said electric heater and extends to said base end of said base body; and a front end of the third metallic terminal is equipped with an urging member configured into a flat plate, a wire, or a curved plate convex to the longitudinal axis of said solid electrolyte, and said urging member equipped at said front end of said third metallic terminal causes a pressing force acting toward said electric heater in a direction which is substantially normal to the longitudinal axis of said solid electrolyte so that said front end of said third metallic terminal is brought into contact with said electric heater.

12. The gas sensor in accordance with claim 11, wherein a cross section of said solid electrolyte is circular at a portion where the front end of said third metallic terminal is resiliently brought into contact with said electric heater.

13. The gas sensor in accordance with claim 9, wherein said gas sensor element is held to said housing, and said urging member equipped at the front end of said first metallic terminal causes a pressing force for resiliently urging said gas sensor element in a direction normal to the longitudinal axis of said solid electrolyte.

14. The gas sensor in accordance with claim 9, wherein a cross section of said solid electrolyte is circular at a portion where the front end of said first metallic terminal and a front end of said second metallic terminal are resiliently brought into contact with said first and second leads, respectively.

15. The gas sensor in accordance with claim 9, wherein front ends of said metallic terminals are rotationally symmetric along a circle surrounding the longitudinal axis of said solid electrolyte.

16. An gas sensor comprising:

a cup-shaped solid electrolyte having an opening at a base end side and a bottom at a front end side, said base end side being exposed to the air and said front end side being exposed to a measuring gas;

a measuring electrode provided on an outer surface of the front end side of said solid electrolyte;

a reference electrode provided on an inner surface of said front end side of said solid electrolyte;

a first lead in electrical contact with said measuring electrode and extending to said base end side of said solid electrolyte;

a second lead in electrical contact with said reference electrode and extending to said base end side of said solid electrolyte;

a housing having a through hole for accommodating said solid electrolyte;

a base body made of a resin and fixed directly to said housing so as to cover the base end side of said solid electrolyte;

a first metallic terminal in electrical contact with said first lead and extending to a base end side of said base body, said first metallic terminal being insert molded together with said resin base body;

a second metallic terminal in electrical contact with said second lead and extending to the base end side of said base body; and a relay plate interposed between said first metallic terminal and said first lead to electrically connect said first metallic terminal to said first lead, and said relay plate being made of a leaf spring causing a resilient force for pressing said first lead.

17. The gas sensor in accordance with claim 16, wherein said second lead is exposed on an outer surface at the base end of said solid electrolyte, and a relay plate is interposed between said second metallic terminal and said second lead to electrically connect said second metallic terminal to said second lead, said relay plate being made of a leaf spring causing a resilient force for pressing said second lead.

18. The gas sensor in accordance with claim 17, wherein an electric heater is located on an outer surface of said solid electrolyte, a third metallic terminal is brought into electrical contact with said electric heater and extends to said base end side of said base body; and a relay plate is interposed between said third metallic terminal and a base end of said electric heater to electrically connect said third metallic terminal to said electric heater, said relay plate being made of a leaf spring causing a resilient force for pressing said electric heater.

19. The gas sensor in accordance with claim 18, wherein the disposition of said relay plates is rotationally symmetric along a circle surrounding the longitudinal axis of said solid electrolyte.

20. The gas sensor in accordance with claim 9 or 16, wherein said measuring electrode is integral with said first lead, and said reference electrode is integral with said second lead.

* * * * *